United States Patent [19]

Tybring

[11] 4,076,816
[45] Feb. 28, 1978

[54] ANTIBIOTIC MIXTURE
[75] Inventor: Leif Tybring, Gentofte, Denmark
[73] Assignee: Leo Pharmaceutical Products Ltd. A/S, Ballerup, Denmark
[21] Appl. No.: 573,453
[22] Filed: May 1, 1975
[30] Foreign Application Priority Data
 May 17, 1974 United Kingdom ............... 22171/74
[51] Int. Cl.² .................... A61K 31/305; A61K 31/43
[52] U.S. Cl. ..................................... 424/251; 424/271
[58] Field of Search ............................... 424/251, 271
[56] References Cited
U.S. PATENT DOCUMENTS
3,755,588 8/1973 Lund .................................... 424/271

OTHER PUBLICATIONS

The Merck Index, 8th Ed., 1968, Merck & Co., Inc., Rahway, N.J. p. 1077.

Primary Examiner—Jerome D. Goldberg
Attorney, Agent, or Firm—Jackson, Jackson & Chovanes

[57] ABSTRACT

The present invention relates to a new pharmaceutical composition with synergistic properties, to dosage units thereof, and to the use of the said composition and dosage units in the human or veterinary practice for the treatment of patients suffering from infectious diseases. The composition contains as active ingredients an amidinopenicillanic acid derivative of the formula

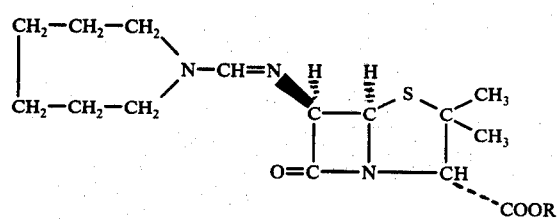

in which R is hydrogen or a lower alkanoyloxymethyl radical including the pivaloyloxymethyl radical or atoxic salts thereof in combination with 2,4-diamino-5(3,4,5-trimethoxybenzyl)-pyrimidine, also known under the name trimethoprim, used hereinafter, or atoxic salts thereof.

13 Claims, No Drawings

ANTIBIOTIC MIXTURE

This invention relates to a new pharmaceutical composition with synergistic properties, to dosage units thereof, and to the use of the said composition and dosage units in the human or veterinary practice for the treatment of patients suffering from infectious diseases. The composition contains as active ingredients an amidinopenicillanic acid derivative of the formula

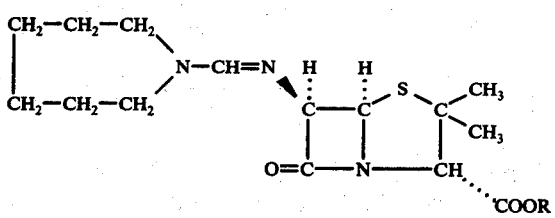

in which R is hydrogen or a lower alkanoyloxymethyl radical including the pivaloyloxymethyl radical or atoxic salts thereof in combination with 2,4-diamino-5(3,4,5-trimethoxybenzyl)-pyrimidine, also known under the name trimethoprim, used hereinafter, or atoxic salts thereof.

Both of the active ingredients in the composition are well-known compounds used in treatment of patients suffering from bacterial diseases. The amidinopenicillanic acid and its esters are prepared as described in the specification to the British Pat. No. 1,293,590. They are useful in the free form and in the form of their atoxic salts. More specifically the invention is concerned either with a composition for oral administration containing an alkanoyloxymethyl ester of the amidinopenicillanic acid and trimethoprim, or a composition for enteral administration containing the first component as free acid or as an atoxic salt thereof and trimethoprim, or a salt thereof. The above alkanoyloxymethyl esters can be used as such or in the form of one of their atoxic salts.

Such salts are especially pharmaceutically acceptable, non-toxic salts with acids such as hydrochloric acid, hydrobromic acid, sulphuric acid, phosphoric acids, p-toluenesulfonic acid, citric acid, maleic acid, etc.

Suitable salts of trimethoprim are especially salts with such acids as mentioned above.

In the compositions according to the invention the usable salts of the amidinopenicillanic acid of the formula I (R=H) include the water-soluble sodium, potassium, ammonium, triethylamine, piperidine, morpholine, cyclohexylamine, and mono- and diethanolamine salts, and the more or less water-soluble calcium, magnesium, dibenzylethylenediamine, benzyl-$\beta$-phenylethylamine, and procaine salts or salts with other antibiotics with acidic or basic characteristics. Among the salts preferred mention may be made of the sodium and diethanolamine salts. Further, the amidinopenicillanic acid itself can be one of the ingredients of the composition.

The attainment of such a synergistic effect by a combined administration of the amidinopenicillanic acid derivatives and trimethoprim is quite unexpected in consideration of the generally accepted circumstances under which such effect will be seen.

In the literature (Antibiotic and Chemotherapy by L. P. Garrod and F. O'Grady, London 1973) is described the three possible types of combined action of two antibacterial drugs. The effect may be simply additive, if the components are both bacteristatic, it may be antagonistic, if the one is bactericidal and the other bacteristatic, or it may be synergistic, if both are bactericidal.

Exceptions are known such as the combination of trimethoprim with sulfa drugs which according to the above citation should simply act additive, but nevertheless show a synergism. This exception is obvious, however, and can be simply explained by the fact that the two components of the mixture act sequentially in the same metabolic pathway. Taking into consideration the many different pathways in the metabolism of the microorganism there is a very small probability of finding such exceptions, in particular when dealing with mixtures expected to act antagonistic.

In the present invention where such antagonistic action was most probable, the components of the mixture act in different pathways in the metabolism, and exceptions from this rule should not been expected, trimethoprim acting on tetrahydrofolate biosynthesis whereas amidinopenicillanic acids have influence on the cell wall.

It has now surprisingly been found in our experiments that a striking synergistic effect was observed as will be seen from the Examples below.

Another advantage of the combined use is a diminished tendency to development of resistent strains of bacteria.

The synergistic effect may be utilized either by a reduction in the employed doses whereby the risk of side effects is diminished or may be utilized in combating less sensitive strains.

The synergistic effect has been observed in a long series of bacteria species, but is especially interesting in species of gram-neg. bacteria, such as *Escherichia coli*, Salmonella, Haemophilus, and Proteus. The in vitro experiments have shown that the ratio of the components in the composition giving rise to the highest degree of synergism depends on both substrate and species.

It should be mentioned, therefore, that in animal experiments or clinical trials, the optimal ratio of the two active components may differ from the ratios of the in vitro experiments, the absorption and excretion rates and the distribution in the body liquids of the active components contained in the composition being factors of importance to the choice of the appropriate ratio between the active ingredients.

In the composition of the invention the ratio of the amidinopenicillanic acid ester to trimethoprim is within the range from 5 to 95 percent.

That is to say that the ratio between the two components goes grom 1:19 to 19:1. Within this range the preferred ratio will in most cases be from 1:10 to 10:1, depending on the infection to be combated and the condition of the patient.

The total amount of active ingredients in the composition lies in the range of from 10 percent to 100 percent of the composition in the case of this being in solid form and intended for oral administration and from 0.5 to 30 percent in the case of the composition being in a liquid form intended for injection.

The compositions according to the invention can furthermore contain solid or liquid pharmaceutical carriers and auxiliary compounds not interacting with the antibiotic substances, in order to obtain compositions which are usable in particular for enteral, but also for parenteral or topical administration.

Pharmaceutical organic or inorganic, solid or liquid carriers suitable for enteral, parenteral or topical administration are e.g. water, gelatine, lactose, starch, magnesium stearate, talc, vegetable and animal oils and fats, benzylalcohol, gums, polyalkylene glycols, petroleum jelly, cocoa butter, lanolin or other known carriers for medicaments which all are suitable as carriers, while stabilizing agents, wetting or emulsifying agents, salts for varying the osmotic pressure or buffers for securing an adequate pH-value of the compositions can be used as auxiliary agents.

The composition produced can either be worked up to pharmaceutical forms of presentation, such as tablets, pills, dragees, or suppositories, or the composition can be filled into medical containers, such as capsules or ampoules or, as far as suspensions or ointments are concerned, they may be filled into bottles, tubes, or similar containers.

Another object of the invention consists in the selection of a dosage unit which may be advantageously employed in the treatment of infectious diseases.

By the term "dosage unit" is meant a unitary, i.e. a single dose capable of being administered to the patients which may be readily handled and packed, remaining as a physically stable unit dose containing either the active material as such, or the active material mixed with solid or liquid diluents or carriers.

If the composition is to be injected a dosage unit is provided including a sealed ampoule, a vial or a similar container containing a parenterally acceptable, aqueous or oily, injectable solution or dispersion of the active material.

In the treatment of patients suffering from infectious diseases the compositions of the invention are conveniently administered in daily doses from 0.4 g to 5 g of the composition containing the components in an appropriate ratio as mentioned hereinbefore.

Appropriately, the daily dose in given in the form of dosage units, e.g. tablets, of which 1–2 tablets are given 2–4 times a day.

Such dosage units for human use can according to the invention contain from 0.1 g to about 0.5 g in total of a mixture consisting essentially of an amidinopenicillanic acid derivative of the general formula I and trimethoprim or the atoxic salts thereof, the ratio being from 1:19 to 19:1 of the active components forming the synergistic mixture.

As a non-limiting example of a dosage unit can be mentioned a tablet containing 200 mg of pivaloyloxymethyl 6-[(hexahydro-1H-azepin-1-yl)-methyleneamino]-penicillanate hydrochloride and 40 mg of trimethoprim together with the necessary carrier and/or auxiliary agents. For adults the dosage may be 1 to 4 of these tablets given 3 to 4 times a day.

It shall be understood, however, that the adequate doses and frequency of administration may vary, depending upon the condition of the patient and the character of the infection, and shall be determined by the medical practioner.

The dosage unit may also according to the invention be in the form of a dry powdered mixture which immediately before use is suspended in a suitable liquid, e.g. water, soft drinks, milk or other drinkable liquid. This form of administration is especially useful in the pediatric therapy. The invention comprises also readily usable suspensions of the active compounds in a suitable pharmaceutical vehicle, selected for instance with a view to their stability.

In suspensions is used the amidinopenicillanic ester in the free form or in the form of one of its slightly or sparingly soluble salts, e.g. the hydroiodide, or the p-toluenesulphonate, which examples shall not be limiting for the invention.

The dosage unit of the invention may furthermore contain other components which may contribute to increasing the scope of utility of the composition contained in the dosage unit in question, e.g. antibacterially active sulfonamides or nitrofuran derivatives; antibiotics which are not absorbable in the gastro-intestinal tract; or sulfamylbenzoic acid derivatives which are capable of delaying the excretion of the antibiotics administered.

The preferred pharmaceutical form of presentation of dosage units is in the form of capsules, pills or tablets for oral administration. With a view to obtain favourable absorption and distribution in the organism of the drugs involved such tablets or pills can be enteric-coated thereby causing a desired liberation in the gastro-intestinal tract.

Furthermore, according to the invention the dosage unit can appropriately be in the form of tablets, the inner core of which contains one or more of the active components with the necessary pharmaceutical auxiliary agents, whereas the outer core contains the other active component(s) together with adequate auxiliary agents, or such double tablets are provided in which the halves contain their respective components(s) under conditions where no interaction between the components can occur.

The invention will now be illustrated by the following, non-limiting Examples in which FL 1060 is 6-[(hexahydro-1H-azepin-1-yl)-methyleneamino]-penicillanic acid, hydrochloride, dihydrate.

EXAMPLE 1

The in vitro activity of FL 1060, trimethoprim, and combinations of the two compounds against *Escherichia coli* (strain Leo HA2) was determined in a serial dilution test.

A fluid medium containing:

| | |
|---|---|
| Yeast extract | 5 g |
| Casein hydrolysate | 15 g |
| Dextrose | 1 g |
| 1-Cystine | 0.05 g |
| Water up to 1000 ml | | and containing the appropriate concentrations of the compounds, or of the combinations of them was inoculated with $10^6$ cells/ml organisms and incubated over night at 37° C. Minimum inhibitory concentrations (MIC) were taken as the lowest concentrations of either of the compounds alone or of a combination of both at which no visible growth occurred.

| MIC µg/ml | | |
|---|---|---|
| FL 1060 | Trimethoprim | FL 1060 + Trimethoprim |
| 0.016 | 100 | 0.005 + 0.16 |
| | | 0.0016 + 1.6 |

EXAMPLE 2

Using the technique described in Example 1 and the same medium with an addition of 10 g of sodium chloride per liter, we found the following MIC values against *Escherichia coli* (Leo HA2):

| MIC μg/ml | | |
|---|---|---|
| FL 1060 | Trimethoprim | FL 1060 + Trimethoprim |
| 50 | >50 | 0.16 + 0.05 |
|  |  | 0.05 + 5.0 |

EXAMPLE 3

Using the technique described in Example 1 and the same medium with an addition of 10 g of sodium chloride per liter, we found the following in vitro activities against *Klebsiella pneumoniae* (Leo HE):

| MIC μg/ml | | |
|---|---|---|
| FL 1060 | Trimethoprim | FL 1060 + Trimethoprim |
| 0.5 | 1.6 | 0.16 + 0.016 |
|  |  | 0.05 + 0.16 |

EXAMPLE 4

Using the technique described in Example 1 and the same medium with an addition of 10 g of sodium chloride per liter we have recorded the following in vitro activities against *Salmonella typhimurium* (Leo HL2):

| MIC μg/ml | | |
|---|---|---|
| FL 1060 | Trimethoprim | FL 1060 + Trimethoprim |
| >100 | >100 | 1.6 + 0.005 |
|  |  | 0.5 + 0.5 |
|  |  | 0.16 + 1.6 |

EXAMPLE 5

Combined activity of FL 1060 and trimethoprim against *Haemophilus influenzae* in vitro.

Serial dilutions of FL 1060 and trimethoprim were performed in "chocolate agar"[x] plates arranged in form of a chess board. Inoculum: 3.5 μl drops containing about 10[7] cells/ml. Incubation: overnight at 36° C.

[x]Caseinhydrolysate (pancreatic) 1.3%, dextrose 0.085%, sodium chloride 0.21%, 1-cystine 0.004%, agar (Oxoid No. 1) 0.6% in distilled water, pH 7.1 after autoclaving, horse blood (defibriated) 5%, yeast extract (Difco) 1.3% (membrane filtered) added at 80° C.

| Strain | MIC (μg/ml) | | |
|---|---|---|---|
|  | FL 1060 | Trimethoprim | FL 1060 + Trimethoprim |
| IX5 | >100 | 1.0 | 0.32 + 0.32 (1:1) |
| IX6 | >100 | 3.2 | 3.2 + 0.32 (10:1) |
| IX14 | >100 | >100 | 1.0 + 3.2 (1:3) |
| IX15 | >100 | >100 | 0.32 + 3.2 (1:10) |

EXAMPLE 6

Capsules, each containing 0.200 g of pivaloyloxymethyl 6-[(hexahydro-1H-azepin-1-yl)-methyleneamino]penicillanate hydrochloride and 0.04 g of trimethoprim are prepared according to the following procedure:

Ingredients:
| | |
|---|---|
| Pivaloyloxymethyl 6-[(hexahydro-1H-azepin-1-yl)-methyleneamino]-penicillanate hydrochloride | 200 g |
| Trimethoprim | 40 g |
| Polyvinyl pyrrolidone | 10 g |
| Magnesium stearate | 4 g |

The pivaloyloxymethyl 6-[(hexahydro-1H-azepin-1-yl)-methyleneamino]-penicillanate hydrochloride and the trimethoprim are mixed and passed through a 20 U.S. Standard mesh sieve. After having been mixed again, the resulting powder is moistened with a solution of polyvinyl pyrrolidone in isopropanol (150 ml). The moistened mixture is granulated by passing it through a 20 U.S. Standard mesh sieve and is afterwards dried by 30° C. For the drying operation, a conventional drying oven with trays, or other suitable drying apparatus, for instance functioning according to the fluidized bed principle, may be applied.

After drying, the granulate is passed through a 25 U.S. Standard mesh sieve and is finally mixed with the magnesium stearate.

The finished granulate is filled into hard gelatine capsules No. 1, each capsule containing about 0.260 g granulate the above ingredients thereby corresponding to 1,000 capsules.

EXAMPLE 7

Tablets, each containing 0.200 g of pivaloyloxymethyl 6-[(hexahydro-1H-azepin-1-yl)-methyleneamino]-penicillanate HCl and 0.020 g of trimethoprim are prepared according to the following procedure:

Ingredients:
| | |
|---|---|
| Pivaloyloxymethyl 6-[(hexahydro-1H-azepin-1-yl)-methyleneamino]-penicillanate HCl | 200 g |
| Trimethoprim | 20 g |
| Polyvinyl pyrrolidone | 10 g |
| Cellulose, microcrystalline | 175 g |
| Starch | 80 g |
| Magnesium stearate | 4 g |

The pivaloyloxymethyl 6-[(hexahydro-1H-azepin-1-yl)-methyleneamino]-penicillanate hydrochloride and the trimethoprim are mixed and passed through a 20 U.S. Standard mesh sieve. After having been mixed again, the resulting powder is moistened with a solution of polyvinyl pyrrolidone in isopropanol (100 ml). The moistened mixture is granulated by passing it through a 20 U.S. Standard mesh sieve and is afterwards dried by 30° C. For the drying operation, a conventional drying oven with trays or other suitable drying apparatus, for instance functioning according to the fluidized bed principle, may be applied.

After drying, the granulate is passed through a 25 U.S. Standard mesh sieve and is afterwards mixed with the microcrystalline cellulose, the starch and the magnesium stearate. The granulate is compressed into tablets, each containing about 0.500 g, by using punches with a diameter of 12 mm, the above ingredients thereby corresponding to 1,000 tablets.

EXAMPLE 8

Following the procedure described in Example 6, a tablet was made up, having the following composition.

Ingredients for 1000 tablets:

-continued

| | |
|---|---|
| Pivaloyloxymethyl 6-[(hexahydro-1H-azepin-1-yl)-methyleneamino]-penicillanate | 250 g |
| Trimethoprim | 100 g |
| Polyvinyl pyrrolidone | 10 g |
| Cellulose, microcrystalline | 175 g |
| Starch | 80 g |
| Magnesium stearate | 5 g |
| Each tablet weighs about 0.625 g | |

EXAMPLE 9

For peroral administration especially useful in the pediatric therapy the following mixture, intended for suspension in water or another drinkable liquid immediately before use, is produced. The mixture consists per dosage, of the following ingredients:

| | |
|---|---|
| Pivaloyloxymethyl 6-[(hexahydro-1H-azepin-1-yl)-methyleneamino]-penicillanate | 100 mg |
| Trimethoprim | 20 mg |
| Methyl cellulose | 10 mg |
| Sugar | 2.5 g |
| Saccharin sodium | 8 mg |
| Aroma | q.s. |

This dosage is intended for being suspended in about 5 ml of a suitable liquid.

What is claimed is:

1. An antibacterial synergistic composition consisting essentially of a mixture of:

An amidinopenicillanic acid derivative of the general formula

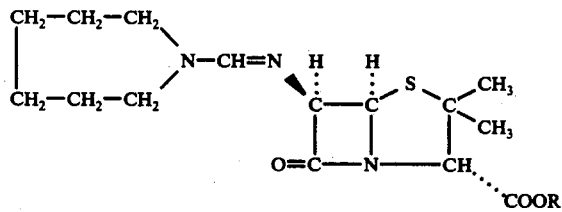

I in which R is hydrogen or lower alkanoyloxymethyl or pharmaceutically acceptable non-toxic salts thereof in combination with trimethoprim, or pharmaceutically acceptable non-toxic salts thereof, which composition contains amounts of the active ingredients so as to provide a ratio of 1:19 to 19:1 when used in the body.

2. A composition as claimed in claim 1, in which the amidino-penicillanic acid derivative is 6-[(hexahydro-1H-azepin-1-yl)-methyleneamino]-penicillanic acid or the pivaloyloxymethyl ester thereof or a pharmaceutically acceptable non-toxic salt of the foregoing acid or ester.

3. A pharmaceutical preparation in dosage unit form for the treatment of patients suffering from bacterial infections, which comprises as an active ingredient from 0.1 g to about 0.5 g in total of a mixture consisting essentially of an amidinopenicillanic acid derivative of formula I of claim 1 or pharmaceutically acceptable non-toxic salts thereof in amounts calculated as the free acid and trimethoprim or pharmaceutically acceptable non-toxic salts thereof, the active components forming the synergistic mixture being present in a ratio of from 1:19 to 19:1.

4. A pharmaceutical preparation in dosage unit form for the treatment of patients suffering from bacterial infections, which comprises as an active ingredient from 0.1 g to about 0.5 in total of a synergistic mixture consisting essentially of 6-[(hexahydro-1H-azepin-1-yl)-methyleneamino]-penicillanic acid, or the pivaloyloxymethyl ester thereof or a pharmaceutically acceptable non-toxic salt of that acid or ester, in an amount calculated as the free acid, and trimethoprim or the pharmaceutically acceptable non-toxic salts thereof, the ratio being from 1:19 to 19:1 of the active components forming the synergistic mixture.

5. A pharmaceutical preparation in dosage unit form in the form of tablets, pills, capsules, or powder for the oral treatment of patients suffering from bacterial infections, which comprises as an active ingredient from 0.1 g to about 0.5 g in total of a synergistic mixture consisting essentially of 6-[(hexahydro-1H-azepin-1-yl)-methyleneamino]-penicillanic acid, or the pivaloyloxymethyl ester thereof or a pharmaceutically acceptable non-toxic salt of that acid or ester, in an amount calculated as the free acid, and trimethoprim or the pharmaceutically acceptable non-toxic salts thereof, the ratio being from 1:19 to 19:1 of the active components forming the synergistic mixture.

6. A pharmaceutical preparation in dosage unit form in the form of tablets, pills, capsules, or powder for the oral treatment of patients suffering from bacterial infections, which comprises as an active ingredient from 0.1 g to about 0.5 in total of a synergistic mixture consisting essentially of 6-[(hexahydro-1H-azepin-1-yl)-methyleneamino]-penicillanic acid, or the pivaloyloxymethyl ester thereof or a pharmaceutically acceptable non-toxic salt of that acid or ester, in an amount calculated as the free acid, and trimethoprim or the pharmaceutically acceptable non-toxic salts thereof, the ratio being from 10:1 to 4:1 of the active components forming the synergistic mixture.

7. A pharmaceutical preparation in dosage unit form in the form of a suspension for the enteral treatment of patients suffering from bacterial infections, which comprises as an active ingredient from 0.1 g to about 0.5 g in total of a synergistic mixture consisting essentially of 6-[(hexahydro-1H-azepin-1-yl)-methyleneamino]-penicillanic acid, or the pivaloyloxymethyl ester thereof or a pharmaceutically acceptable non-toxic salt of that acid or ester, in an amount calculated as the free acid, and trimethoprim or the pharmaceutically acceptable non-toxic salts thereof, which composition contains amounts of the active ingredients so as to provide a ratio of 1:19 to 19:1 when used in the body, and the active components being in association with a pharmaceutically acceptable carrier.

8. The method of treating patients suffering from bacterial infections which comprises administering by the oral route to the patients, in antibacterially effective amounts, dosage units of a synergistic composition according to claim 1 containing a compound of formula I of claim 1 in which R is alkanoyloxymethyl or its pharmaceutically acceptable non-toxic salts, which composition contains amounts of the active ingredients so as to provide a ratio of 1:19 to 19:1 when used in the body.

9. The method of treating patients suffering from bacterial infections, which comprises administering to the patient a synergistic mixture in a daily dose of from 0.4 g to 5 g in total of: (1) an amidinopenicillanic acid derivative of the formula I -continued

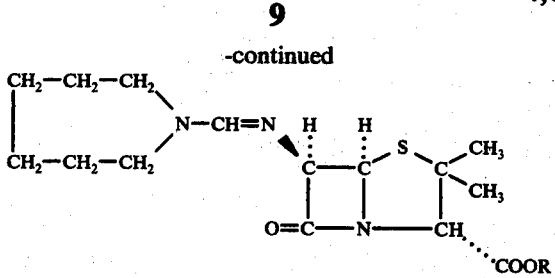

in which R is hydrogen or lower alkanoyloxymethyl or pharmaceutically acceptable non-toxic salts thereof and trimethoprim or pharmaceutically acceptable non-toxic salts thereof, which composition contains amounts of the active ingredients so as to provide a ratio of 1:19 to 19:1 when used in the body.

10. The method of treating patients suffering from bacterial infections, which comprises administering to the patient a synergistic mixture in a daily dose of from 0.4 to 5 g in total of: (1) of amidinopenicillanic acid derivative of the formula

I

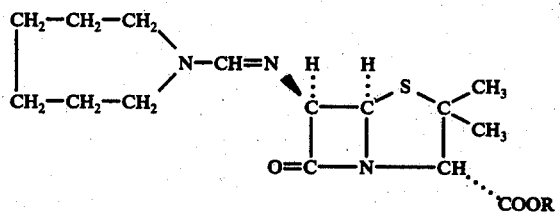

in which R is hydrogen of lower alkanoyloxymethyl or pharmaceutically acceptable non-toxic salts thereof and trimethoprim or pharmaceutically acceptable non-toxic salts thereof, which composition contains amounts of the active ingredients so as to provide a ratio of 10:1 to 4:1 when used in the body.

11. A method for the treatment of bacterial infections in a patient, comprising simultaneous administration to a patient suffering from a bacterial infection of a compound of formula I of claim 1 and trimethoprim, the said compound of formula I and trimethoprim being in a ratio of from 1:19 to 19:1, and in amounts which are antibacterially effective when so administered, said compounds acting synergistically in the body fluids.

12. A method for the treatment of bacterial infections in a patient, comprising sequentially administering to a patient suffering from a bacterial infection a compound of formula I of claim 1 and trimethoprim, the said compound of formula I and trimethoprim being in a ratio of from 1:19 to 19:1 and in amounts which are antibacterially effective when so administered, said compounds acting synergistically in the body fluids.

13. The method of treating patients suffering from bacterial infections which comprises administering by the parenteral route to the patients, in antibacterially effective amounts, dosage units of an antibacterial synergistic composition consisting essentially of a mixture of:

An amidinopenicillanic acid derivative of the general formula

I

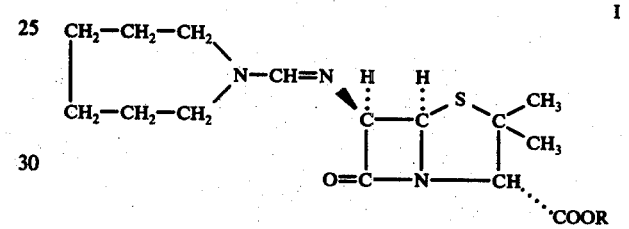

in which R is hydrogen, or its pharmaceutically acceptable non-toxic salts, in combination with trimethoprim, or pharmaceutically acceptable non-toxic salts thereof, which composition contains amounts of the active ingredients so as to provide a ratio of 1:19 to 19:1 when used in the body.

* * * * *